(12) United States Patent
Walke et al.

(10) Patent No.: US 7,374,933 B2
(45) Date of Patent: May 20, 2008

(54) HUMAN METALLOPROTEASE AND POLYNUCLEOTIDES ENCODING THE SAME

(75) Inventors: D. Wade Walke, Spring, TX (US); Nathaniel L. Wilganowski, Houston, TX (US); C. Alexander Turner, Jr., The Woodlands, TX (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 1565 days.

(21) Appl. No.: 09/833,782

(22) Filed: Apr. 12, 2001

(65) Prior Publication Data

US 2002/0040131 A1 Apr. 4, 2002

Related U.S. Application Data

(60) Provisional application No. 60/196,319, filed on Apr. 12, 2000.

(51) Int. Cl.
*C12N 9/64* (2006.01)
*C12N 15/00* (2006.01)
*C12N 5/00* (2006.01)
*C12N 1/12* (2006.01)
*C07H 21/04* (2006.01)

(52) U.S. Cl. .................. 435/325; 435/320.1; 435/226; 435/252.1; 536/23.2

(58) Field of Classification Search ............... 536/23.2; 435/212, 195, 320.1, 252.1, 325, 226
See application file for complete search history.

(56) References Cited

FOREIGN PATENT DOCUMENTS

WO    WO 01/23590 A2    4/2001

OTHER PUBLICATIONS

Kato A. et al, Targeting of Endopeptidase 24.16 to Different Subcellular Compartments by Alternative Promoter Usage, J. Biol. Chem. 1997, 272/24, 15313-15322.*

Serizawa A. Characterization of a Mitochondrial Metallopeptidase Reveals Neurolysin as a Homologue of Thimet Oligopeptidase, J. Biol. Chem. 1995, 270, 2092-2098.*

Database EMBL 'Online, ' entry/acc. No. AW003054, Sep. 9, 1999. Strausberg, R., "wq61h05.x1 NCI_CGAP_GC6 *Homo sapiens* cDNA clone Image: 2475801 3' similar to SW:NEUL_PIG Q02038 Neurolysin Precursor: mRNA sequence," XP002171872.

Nagase, Takahiro, et al., "Prediction of the Coding Sequences of Unidentified Human Genes. XV. The Complete Sequences of 100 New (cDNA Clones from Brain which Code for Large Proteins in vitro," *DNA Research*, Universal Academy Press, JP, vol. 6, 1999, pp. 337-345, XP000865804.

Sugiura, Naoaki, et al., "Molecular Cloning of Porcine Soluble Angiotensin-binding Protein," *Journal of Biological Chemistry*, vol. 267, No. 25, 1992, pp. 18067-18072, XP002171869.

Kawabata, Shun-ichiro, et al., "Rabbit Liver Microsomal Endopeptidase with Substrate Specificity for Processing Proproteins is Structually Related to Rat testes Metalloendopeptidase 24.15," *Journal of Biological Chemistry*, vol. 268, No. 17, 1993, pp. 12498-12503, XP002171870.

Dauch, Pascale, et al., "Molecular Cloning and Expression of Rat Brain Endopeptidase 3.4.24.16," *Journal of Biological Chemistry*, vol. 270, No. 45, 1995, pp. 27266-27241, XP002171871.

Krause, Darren R., et al., "Characterization and Localization of Mitochondrial Oligopeptidase (MOP) (EC 3.4.24.16) Activity in the Human Cervical Adenocarcinoma Cell Line HeLa," *Journal of Cellular Biochemistry*, vol. 66, No. 3, 1997, pp. 297-308, XP002172752.

Vincent, B. et al., "Purification and Characterization of human endopeptidase 3.4.24.16. Comparison with the procrine counterpart indicates a unique cleavage site on neurotensin, " *Brain Research*, vol. 709, No. 1, 1996, pp. 51-58, XP001010406.

Database EMBL 'Online, ' Entry HSA300837, Acc. No. AJ300837, Jan. 26, 2001, Chen, J.M. et al., "*Homo sapiens* mRNA for neurolysin," XP002171897.

* cited by examiner

*Primary Examiner*—Rebecca Prouty
*Assistant Examiner*—M. A. Walicka
(74) *Attorney, Agent, or Firm*—Lance K Ishimoto; Peter G Seferian

(57) ABSTRACT

Novel human polynucleotide and polypeptide sequences are disclosed that can be used in thereapeutic, diagnostic, and pharmacogenomic applications.

4 Claims, No Drawings

SEQUENCE LISTING

```
<160> NUMBER OF SEQ ID NOS: 3

<210> SEQ ID NO 1
<211> LENGTH: 2115
<212> TYPE: DNA
<213> ORGANISM: homo sapiens

<400> SEQUENCE: 1
atgatcgccc ggtgcctttt ggctgtgcga agcctccgca gagttggtgg ttccaggatt      60
ttactcagaa tgacgttagg aagagaagtg atgtctcctc ttcaggcaat gtcttcctat     120
actgtggctg gcagaaatgt tttaagatgg gatctttcac cagagcaaat taaaacaaga     180
actgaggagc tcattgtgca gaccaaacag gtgtacgatg ctgttggaat gctcggtatt     240
gaggaagtaa cttacgagaa ctgtctgcag gcactggcag atgtagaagt aaagtatata     300
gtggaaagga ccatgctaga ctttccccag catgtatcct ctgacaaaga agtacgagca     360
gcaagtacag aagcagacaa aagactttct cgttttgata ttgagatgag catgagagga     420
gatatatttg agagaattgt tcatttacag gaaacctgtg atctggggaa gataaaacct     480
gaggccagac gatacttgga aaagtcaatt aaaatgggga aaagaaatgg gctccatctt     540
```

```
cctgaacaag tacagaatga atcaaatca atgaagaaaa gaatgagtga gctatgtatt    600
gattttaaca aaacctcaa tgaggatgat accttccttg tattttccaa ggctgaactt    660
ggtgctcttc ctgatgattt cattgacagt ttagaaaaga cagatgatga caagtataaa    720
attaccttaa aatatccaca ctatttccct gtcatgaaga aatgttgtat ccctgaaacc    780
agaagaagga tggaaatggc ttttaataca aggtgcaaag aggaaaacac cataattttg    840
cagcagctac tcccactgcg aaccaaggtg gccaaactac tcggttatag cacacatgct    900
gacttcgtcc ttgaaatgaa cactgcaaag agcacaagcc gcgtaacagc ytttctagat    960
gatttaagcc agaagttaaa acccttgggt gaagcagaac gagagtttat tttgaatttg   1020
aagaaaaagg aatgcaaaga caggggtttt gaatatgatg ggaaaatcaa tgcctgggat   1080
ctatattact acatgactca gacagaggaa ctcaagtatt ccatagacca agagttcctc   1140
aaggaatact tcccaattga ggtggtcact gaaggcttgc tgaacaccta ccaggagttg   1200
ttgggacttt catttgaaca aatgacagat gctcatgttt ggaacaagag tgttacactt   1260
tatactgtga aggataaagc tacaggagaa gtattgggac agttctattt ggacctctat   1320
ccaagggaag gaaatacaa tcatgcggcc tgcttcggtc tccagcctgg ctgccttctg   1380
cctgatggaa gccggatgat ggcagtggct gccctcgtgg tgaacttctc acagccagtg   1440
gcaggtcgtc cctctctcct gagacacgac gaggtgagga cttactttca tgagtttggt   1500
cacgtgatgc atcagatttg tgcacagact gattttgcac gatttagcgg aacaaatgtg   1560
gaaactgact ttgtagaggt gccatcgcaa atgcttgaaa attgggtgtg ggacgtcgat   1620
tccctccgaa gattgtcaaa acattataaa gatggaagcc ctattgcaga cgatctgctt   1680
gaaaaacttg ttgcttctag gctggtcaac acaggtcttc tgaccctgcg ccagattgtt   1740
ttgagcaaag ttgatcagtc tcttcatacc aacacatcgc tggatgctgc aagtgaatat   1800
gccaaatact gctcagaaat attaggagtt gcagctactc caggcacaaa tatgccagct   1860 accttttggac atttggcagg gggatacgat ggccaatatt atggatatct ttggagtgaa   1920
gtattttcca tggatatgtt ttacagctgt tttaaaaaag aagggataat gaatccagag   1980
gttggaatga aatacagaaa cctaatcctg aaacctgggg gatctctgga cggcatggac   2040
atgctccaca atttcttgaa acgtgagcca aaccaaaaag cgttcctaat gagtagaggc   2100
ctgcatgcty cgtga                                                    2115
```

<210> SEQ ID NO 2
<211> LENGTH: 704
<212> TYPE: PRT
<213> ORGANISM: homo sapiens

<400> SEQUENCE: 2

```
Met Ile Ala Arg Cys Leu Leu Ala Val Arg Ser Leu Arg Arg Val Gly
 1               5                  10                  15

Gly Ser Arg Ile Leu Leu Arg Met Thr Leu Gly Arg Glu Val Met Ser
             20                  25                  30

Pro Leu Gln Ala Met Ser Ser Tyr Thr Val Ala Gly Arg Asn Val Leu
         35                  40                  45

Arg Trp Asp Leu Ser Pro Glu Gln Ile Lys Thr Arg Thr Glu Glu Leu
     50                  55                  60

Ile Val Gln Thr Lys Gln Val Tyr Asp Ala Val Gly Met Leu Gly Ile
 65                  70                  75                  80

Glu Glu Val Thr Tyr Glu Asn Cys Leu Gln Ala Leu Ala Asp Val Glu
                 85                  90                  95
```

```
Val Lys Tyr Ile Val Glu Arg Thr Met Leu Asp Phe Pro Gln His Val
            100                 105                 110

Ser Ser Asp Lys Glu Val Arg Ala Ala Ser Thr Glu Ala Asp Lys Arg
            115                 120                 125

Leu Ser Arg Phe Asp Ile Glu Met Ser Met Arg Gly Asp Ile Phe Glu
            130                 135                 140

Arg Ile Val His Leu Gln Glu Thr Cys Asp Leu Gly Lys Ile Lys Pro
145                 150                 155                 160

Glu Ala Arg Arg Tyr Leu Glu Lys Ser Ile Lys Met Gly Lys Arg Asn
                165                 170                 175

Gly Leu His Leu Pro Glu Gln Val Gln Asn Glu Ile Lys Ser Met Lys
            180                 185                 190

Lys Arg Met Ser Glu Leu Cys Ile Asp Phe Asn Lys Asn Leu Asn Glu
            195                 200                 205

Asp Asp Thr Phe Leu Val Phe Ser Lys Ala Glu Leu Gly Ala Leu Pro
            210                 215                 220

Asp Asp Phe Ile Asp Ser Leu Glu Lys Thr Asp Asp Lys Tyr Lys
225                 230                 235                 240

Ile Thr Leu Lys Tyr Pro His Tyr Phe Pro Val Met Lys Lys Cys Cys
                245                 250                 255

Ile Pro Glu Thr Arg Arg Met Glu Met Ala Phe Asn Thr Arg Cys
            260                 265                 270

Lys Glu Glu Asn Thr Ile Ile Leu Gln Gln Leu Leu Pro Leu Arg Thr
            275                 280                 285

Lys Val Ala Lys Leu Leu Gly Tyr Ser Thr His Ala Asp Phe Val Leu
            290                 295                 300

Glu Met Asn Thr Ala Lys Ser Thr Ser Arg Val Thr Ala Phe Leu Asp
305                 310                 315                 320

Asp Leu Ser Gln Lys Leu Lys Pro Leu Gly Glu Ala Glu Arg Glu Phe
                325                 330                 335

Ile Leu Asn Leu Lys Lys Lys Glu Cys Lys Asp Arg Gly Phe Glu Tyr
            340                 345                 350

Asp Gly Lys Ile Asn Ala Trp Asp Leu Tyr Tyr Met Thr Gln Thr
            355                 360                 365

Glu Glu Leu Lys Tyr Ser Ile Asp Gln Glu Phe Leu Lys Glu Tyr Phe
            370                 375                 380

Pro Ile Glu Val Val Thr Glu Gly Leu Leu Asn Thr Tyr Gln Glu Leu
385                 390                 395                 400

Leu Gly Leu Ser Phe Glu Gln Met Thr Asp Ala His Val Trp Asn Lys
                405                 410                 415

Ser Val Thr Leu Tyr Thr Val Lys Asp Lys Ala Thr Gly Glu Val Leu
            420                 425                 430

Gly Gln Phe Tyr Leu Asp Leu Tyr Pro Arg Glu Gly Lys Tyr Asn His
            435                 440                 445

Ala Ala Cys Phe Gly Leu Gln Pro Gly Cys Leu Leu Pro Asp Gly Ser
            450                 455                 460

Arg Met Met Ala Val Ala Ala Leu Val Val Asn Phe Ser Gln Pro Val
465                 470                 475                 480

Ala Gly Arg Pro Ser Leu Leu Arg His Asp Glu Val Arg Thr Tyr Phe
                485                 490                 495

His Glu Phe Gly His Val Met His Gln Ile Cys Ala Gln Thr Asp Phe
            500                 505                 510
```

```
Ala Arg Phe Ser Gly Thr Asn Val Glu Thr Asp Phe Val Glu Val Pro
        515                 520                 525

Ser Gln Met Leu Glu Asn Trp Val Trp Asp Val Asp Ser Leu Arg Arg
        530                 535                 540

Leu Ser Lys His Tyr Lys Asp Gly Ser Pro Ile Ala Asp Asp Leu Leu
545                 550                 555                 560

Glu Lys Leu Val Ala Ser Arg Leu Val Asn Thr Gly Leu Leu Thr Leu
                565                 570                 575

Arg Gln Ile Val Leu Ser Lys Val Asp Gln Ser Leu His Thr Asn Thr
            580                 585                 590

Ser Leu Asp Ala Ala Ser Glu Tyr Ala Lys Tyr Cys Ser Glu Ile Leu
        595                 600                 605

Gly Val Ala Ala Thr Pro Gly Thr Asn Met Pro Ala Thr Phe Gly His
        610                 615                 620

Leu Ala Gly Gly Tyr Asp Gly Gln Tyr Tyr Gly Tyr Leu Trp Ser Glu
625                 630                 635                 640

Val Phe Ser Met Asp Met Phe Tyr Ser Cys Phe Lys Lys Glu Gly Ile
                645                 650                 655

Met Asn Pro Glu Val Gly Met Lys Tyr Arg Asn Leu Ile Leu Lys Pro
            660                 665                 670

Gly Gly Ser Leu Asp Gly Met Asp Met Leu His Asn Phe Leu Lys Arg
        675                 680                 685

Glu Pro Asn Gln Lys Ala Phe Leu Met Ser Arg Gly Leu His Ala Pro
        690                 695                 700

<210> SEQ ID NO 3
<211> LENGTH: 6306
<212> TYPE: DNA
<213> ORGANISM: homo sapiens

<400> SEQUENCE: 3
cgtgatcttg gctcactgca gcctctgcct ccytggttca agcgattctc ctgcttcagc    60
cacctgatgc ctcagacagt ggttcaaatt aatacgactc actataggga gacttctttc   120
tcccatttca ggtgtcgtaa gcttgaattc aataactata acggtcctaa ggtagcgaag   180
tctcagcgct cccatgatcg cccggtgcct tttggctgtg cgaagcctcc gcagagttgg   240
tggttccagg attttactca gaatgacgtt aggaagagaa gtgatgtctc ctcttcaggc   300
aatgtcttcc tatactgtgg ctggcagaaa tgttttaaga tgggatcttt caccagagca   360
aattaaaaca gaactgaggg agctcattgt gcagaccaaa caggtgtacg atgctgttgg   420
aatgctcggt attgaggaag taacttacga gaactgtctg caggcactgg cagatgtaga   480
agtaaagtat atagtggaaa ggaccatgct agactttccc cagcatgtat cctctgacaa   540
agaagtacga gcagcaagta cagaagcaga caaaagactt tctcgttttg atattgagat   600
gagcatgaga ggagatatat ttgagagaat tgttcattta caggaaacct gtgatctggg   660
gaagataaaa cctgaggcca gacgatactt ggaaaagtca attaaaatgg ggaaaagaaa   720
tgggctccat cttcctgaac aagtacgaa tgaaatcaaa tcaatgaaga aaagaatgag   780
tgagctatgt attgatttta caaaaaacct caatgaggat gataccttcc ttgtattttc   840
caaggctgaa cttggtgctc ttcctgatga tttcattgac agtttagaaa agacagatga   900
tgacaagtat aaaattacct taaaatatcc acactatttc cctgtcatga gaaatgttg   960 tatccctgaa accagaagaa ggatggaaat ggctttaat acaaggtgca aagaggaaaa  1020
caccataatt ttgcagcagc tactcccact gcgaaccaag gtggccaaac tactcggtta  1080
```

```
tagcacacat gctgacttcg tccttgaaat gaacactgca aagagcacaa gccgcgtaac    1140
agcytttcta gatgatttaa gccagaagtt aaaacccttg ggtgaagcag aacgagagtt    1200
tattttgaat ttgaagaaaa aggaatgcaa agacaggggt tttgaatatg atgggaaaat    1260
caatgcctgg gatctatatt actacatgac tcagacagag gaactcaagt attccataga    1320
ccaagagttc ctcaaggaat acttcccaat tgaggtggtc actgaaggct tgctgaacac    1380
ctaccaggag ttgttgggac tttcatttga acaaatgaca gatgctcatg tttggaacaa    1440
gagtgttaca ctttatactg tgaaggataa agctacagga gaagtattgg acagttcta     1500 tttggacctc tatccaaggg aaggaaaata caatcatgcg gcctgcttcg gtctccagcc    1560
tggctgcctt ctgcctgatg gaagccggat gatggcagtg gctgccctcg tggtgaactt    1620
ctcacagcca gtggcaggtc gtccctctct cctgagacac gacgaggtga ggacttactt    1680
tcatgagttt ggtcacgtga tgcatcagat ttgtgcacag actgattttg cacgatttag    1740
cggaacaaat gtggaaactg actttgtaga ggtgccatcg caaatgcttg aaaattgggt    1800
gtgggacgtc gattccctcc gaagattgtc aaaacattat aaagatggaa gcccctattgc   1860 agacgatctg cttgaaaaac ttgttgcttc taggctggtc aacacaggtc ttctgacccct    1920 gcgccagatt gttttgagca agttgatca gtctcttcat accaacacat cgctggatgc     1980
tgcaagtgaa tatgccaaat actgctcaga aatattagga gttgcagcta ctccaggcac    2040
aaatatgcca gctacctttg gacatttggc aggggggatac gatggccaat attatggata   2100
tctttggagt gaagtatttt ccatggatat gttttacagc tgttttaaaa aagaagggat    2160
aatgaatcca gaggttggaa tgaaatacag aaacctaatc ctgaaacctg ggggatctct    2220
ggacggcatg gacatgctcc acaatttctt gaaacgtgag ccaaaccaaa aagcgttcct    2280
aatgagtaga ggcctgcatg ctycgtgaac tggggatctt tggtagccgt ccatgtctgg    2340
aggacaagtc gacatcacca tgtgttactg gcctggaaac tgaagggagt tttgcaagtg   2400
aaaatttaga tttctattga catccttttg ttttctaatt ttaaaaatta taaagatgta    2460
aatggaatta taaatactgt gacctaagaa aagacccact agaaagtaat tgtactataa    2520
aatttcataa aactggattt gatttctttt tatgaaagtt tcatatgaat gtaacttgat    2580
tttttactat tataatctag ataatatgat ataagagggc taagaatttt taaattgaat    2640
catatatatg atataatttg atccttcttg tatcttgaag ttttgtactt gggatttctg    2700
gactgataaa tgaatcatca cattcttctg gtaaatattt tcttggagct ctgtgtcaac    2760
tttgatcctt tgtctcccag gaaggtgtga cctctccttt gcctgcatac ctcaaggcca    2820
ggggaatatg cctcagtgat gcatttatct ttgtatatca ggccgcatga ttcccaactt    2880
tctgccacac ttaaattacg ttcctccatt tcagttttgt cttttctgtc taaagttcag    2940
tcaaagagta tcaaaaaatt atgtttcagc tagactggtg taatgtataa gtttttgtat    3000
cttgtattag aggatttcgt agcttttatt agaggctcat ttccacctca gcatacaaga    3060
tcgttagtct tttggcatgt gtgccaatta gaatactaaa gcaagtccaa gcacattttt    3120
ctcttctcac gtttctaata agtgttaggg actttgcctc ttttacttac cacgtcccca    3180
aaagtgtcag gtagacatgt cacaaatggc tctgtagaga gccatgggaa gagagaggag    3240
gtggatgtgg aacataaagg gttcagaaac tccagaagag gagtgggttt tggatagaag    3300
catttgagga cagctgctcc aaagcctat gtgtatgatg aaacttaacc acggggaaga     3360
gactcttcag tagcctgttc tgtctggtga ttttattttt aagtgaacct ttggatctat    3420
```

```
ctttaactct ctttattgtg agtctaaatt ccaattctgc agcagatcag taaactcaca    3480 gtattttcc tgtggaaatc tattcaataa ggaaaccaag acaggataat aaaatttaaa     3540
aaaaaaacaa ctttgaattc ccctgcctag gtcttccagt tgttttccag cgcatacctc    3600
aggtatgact ttgctagccg gggacaaaat tagcaccttc cgattctcta gtccaaatga    3660
actttgtgct aaataaaaaa ttattatact acataataaa gttacagata gcaggaaatg    3720
caagagctag gagattccta gattatatct gccaagcaaa taccttaaac atccacctga    3780
aatcctacta cccccctcttc tgagataatt tgcccagccc ttctcttccc acacactcac    3840
tcaatgtcac cccccttctaa tccccaaaac tgttttttgtg gtctttgtag cctatagtag   3900
ttttctcaca tctttccccc tagacttttc tgttttttcag tttcagacaa aaaaactctt   3960 cagcttttc cagtgtgtct ccttaacagt aactttacca cttgaaatct tatttcatag     4020
aaaaactaaa ttggtgtgga aaggctgcac acaataaagt tatattatta tccatgaaaa    4080
tgaactcata tttctttcat actttaacgt taaaaccgaa atgcatgaga gcaaaagcac    4140
catggtgttc tttctattta gggcctacct ctaatattta aaatctacca aagagcagtc    4200
acaaaattaa aactcagccc gggcgcagtg gctcatgcct gtaatcccag cactttggga    4260
ggccaaggca ggaggatcac ctgaggtcag agttcaagac cagcatggtc aacatggtga    4320
aaccctgtct ctacaaaaat acaaaaagct gggcatgatg ttgggttcct gtagtcccag    4380
ctacttagga ggctgaggca ggagaatagc ttgaacccgg gaggtggagg ttgcagtgag    4440
ctgagatcat gccattgcac tccagcctgg acgacagagt gagattcagt ctcaaaaaaa    4500
attaatactc aaagaattat ctagcataat ttaaaagaaa ggactttttta aaaattctct    4560 agcataattc aaaagaaagg acttaacttt tttttttttt tagtgtggtc atccgtctag    4620
ttgttctttt tttccagatc agagcagaga atatcactga catgcttgaa atggtggata    4680
actatgtaaa ttgtaattgg acaaatgtac actttagatt tatggactga gcccacatata    4740 ataaggtctc tcctggtaat tgatccaggg gatttaggcc tctttcgggt ttttttgtttt   4800 ttttttaggc attgttatgt tgtgaaggat aaaatcttca acatcttatg caaatggata    4860
gtaggcatga tcctaaaggt ttagttttac gatgctgcag agaagagaaa tgtcttgacg    4920
ttttgccacc tgatgtagac tttgtccccc tctagtataa atgttgcatg ttacctagat    4980
aaacaactaa aaattgcctt gagttatcac ctgagctact tatgccaagg tcttgccttt    5040
ctaaagctaa taaggtgaga ggtggatatc tgtagctctt cggatgaaaa attgcattgt    5100
gggagatacc aaaattgagg aaatagctct tcaaagaaaa attactgata tgatcattgt    5160
acttgtaaat gccttaagta gcaggcagtg actcaattt ctactttacc attttacctt     5220
tagcttttat gtatgaatta taggtctgtg gagattctgc ctccccacta ggccagtgtg    5280
tgtttaccat ttattcattt tctatcatac acaggtggat taaaatttac attaaaattt    5340
acattaaaat accatcatac ttcaggcttc tataacaaaa tatcagactg ggtggcttca    5400
aaagcagaca tttcttacag ttctggaagc tgggaagtcc cacaatccac atgctggtaa    5460
atttggttcg tggtgaggcc cctcttcctc ttttactgac cacatcccca aaagtgtcag    5520
gtagacatgt tacaaatagc tctgtagaga gccatgggaa gagacaggag gcagatgtgg    5580
aacataaagg gtttagaaac ttctgcaggc agcagtggca gggagcaagc cctagagtgt    5640 ctcttttac gagagcagga atcccatcat gagagttcct tcctcatgac tttatctaaa    5700
cccagtcacc cccaacaaag gccccacccc ctaaccccat cacattggct gttacgcgtt    5760
caatgtaggg gatggggcac aaacattcag tccataacga atactgattc ctcaaatagg   5820
```

```
gtttaaacat agttaactga gcccccaaag aatgttaaaa gagaaaatcc attttatttg    5880
aatagatgca gtgaccacag cttcttccct caaatcaaca cattacagtt agatgtctcc    5940
catctgaaat tggatagccc actgaaattg aacatgcctt ctcttataaa tgtgtggtga    6000
gaataaaagc aacaaagaaa tgaatgtggt ggctcacacc tgtaatccta acactttgga    6060
aggttgaggc aggaggatcc tttgtgctca agagtttgag accagcctga gcaacacagt    6120
gagaccctgt ctctacaaaa actaaaaaaa ttagctaggg atggtggcac atgcctgtag    6180
tcccagctac ttgggaggct gaggtgggag gattgcttga gcccaagaag gtcaaggctg    6240
ccatgagcca taatcacgcc actgcactcc agcctgggtg acagagaccc tgtcttaaaa    6300
taaaat                                                              6306
```

US 7,374,933 B2

HUMAN METALLOPROTEASE AND POLYNUCLEOTIDES ENCODING THE SAME

The present application claims the benefit of U.S. Provisional Application No. 60/196,319 which was filed on Apr. 12, 2000 and is herein incorporated by reference in its entirety.

1. INTRODUCTION

The present invention relates to the discovery, identification, and characterization of novel human polynucleotides encoding a protein sharing sequence similarity with mammalian neurolysin proteins. The invention encompasses the described polynucleotides, host cell expression systems, the encoded proteins, fusion proteins, polypeptides and peptides, antibodies to the encoded proteins and peptides, and genetically engineered animals that either lack or over express the disclosed polynucleotides, antagonists and agonists of the proteins, and other compounds that modulate the expression or activity of the proteins encoded by the disclosed polynucleotides that can be used for diagnosis, drug screening, clinical trial monitoring, the treatment of physiological disorders or diseases, and cosmetic or nutriceutical applications.

2. BACKGROUND OF THE INVENTION

Neurolysins are soluble proteins of the zinc metalloprotease family that bind and cleave protein substrates such as angiotensin or neurotensin (typically between pro and tyr residues). As such, neurolysins have been implicated in a number of biological processes and anomalies such as blood pressure regulation, kidney function, pain management, cardiac disease, natriuresis and diabetes. Consequently, neurolysins can act as therapeutics as well as drug targets.

3. SUMMARY OF THE INVENTION

The present invention relates to the discovery, identification, and characterization of nucleotides that encode a novel human protein, and the corresponding amino acid sequence of this protein. The novel human protein (NHP) described for the first time herein shares structural similarity with animal neurolysins and angiotensin-binding proteins. The novel human nucleic acid sequences described herein, encode a protein/open reading frame (ORF) of 704 amino acids in length (see SEQ ID NO:1).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP polynucleotides (e.g., expression constructs that place the described polynucleotide under the control of a strong promoter system), and transgenic animals that express a NHP transgene, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPS. When the unique NHP sequences described in SEQ ID NOS:1-3 are "knocked-out" they provide a method of identifying phenotypic expression of the particular gene as well as a method of assigning function to previously unknown genes. Additionally, the unique NHP sequences described in SEQ ID NOS:1-3 are useful for the identification of coding sequence and the mapping a unique gene to a particular chromosome.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of a NHP ORF that encodes the described NHP amino acid sequence. SEQ ID NO:3 describes a NHP ORF and flanking regions.

5. DETAILED DESCRIPTION OF THE INVENTION

The NHP described for the first time herein is a novel protein that is expressed in, inter alia, human fetal brain, brain, cerebellum, spinal cord, thymus, trachea, kidney, fetal liver, liver, prostate, testis, adrenal gland, pancreas, salivary gland, stomach, small intestine, colon, skeletal muscle, uterus, mammary gland, esophagus, bladder, cervix, rectum, pericardium, hypothalamus, and gene trapped human cell lines.

The present invention encompasses the nucleotides presented in the Sequence Listing, host cells expressing such nucleotides, the expression products of such nucleotides, and: (a) nucleotides that encode mammalian homologs of the described polynucleotide, including the specifically described NHP, and related NHP products; (b) nucleotides that encode one or more portions of the NHP corresponding to NHP functional domain(s), and the polypeptide products specified by such nucleotide sequences, including but not limited to the novel regions of any active domain(s); (c) isolated nucleotides that encode mutant versions, engineered or naturally occurring, of the described NHP in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing. As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68°

C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequence.

Additionally contemplated are polynucleotides encoding NHP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1-3 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1-3, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1-3 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1-3.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1-3 provides detailed information about transcriptional changes involved in a specific pathway, potentially leading to the identification of novel components or gene functions that manifest themselves as novel phenotypes.

Probes consisting of sequences first disclosed in SEQ ID NOS:1-3 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1-3 can be utilized in microarrays or other assay formats, to screen collections of genetic material from patients who have a particular medical condition. These investigations can also be carried out using the sequences first disclosed in SEQ ID NOS:1-3 in silico and by comparing previously collected genetic databases and the disclosed sequences using computer software known to those in the art.

Thus the sequences first disclosed in SEQ ID NOS:1-3 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS:1-3. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relatve to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or any combination or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625-6641). The oligonucleotide is a 2'-0-methylribonucleotide (Inoue et al., 1987, Nucl. Acids Res. 15:6131-6148), or a chimeric RNA-DNA analogue (Inoue et al., 1987, FEBS Lett. 215:327-330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448-7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene. The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene, such as, for example, testis tissue). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, an inflammatory disorder, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor, N.Y.)

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which a NHP coding sequence is operatively associated with expression control elements such as promoters, promoter/enhancers, etc.).

The NHP or NHP peptides, NHP fusion proteins, NHP nucleotide sequences, antibodies, antagonists and agonists can be useful for the detection of mutant NHPs or inappropriately expressed NHPs for the diagnosis of disease. The NHP or NHP peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for a NHP, but can also identify compounds that trigger NHP-mediated activities or pathways.

Finally, the NHP products can be used as therapeutics. For example, soluble derivatives such as a mature NHP, or NHP peptides/domains corresponding to the NHP, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Soluble NHP can also be modified by proteolytic cleavage to active peptide products (e.g., any novel peptide sequence initiating at any one of the amino acids presented in the Sequence Listing and ending at any downstream amino acid). Such products or peptides can be further subject to modification such as the construction of NHP fusion proteins and/or can be derivatized by being combined with pharmaceutically acceptable agents such as, but not limited to, polyethylene glycol (PEG).

Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding a functional NHP, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 THE NHP SEQUENCES

The cDNA sequence (SEQ ID NO: 1) and the corresponding deduced amino acid sequence (SEQ ID NO: 2) of the described NHP are presented in the Sequence Listing. The NHP nucleotides were obtained by aligning human EST sequences and cDNA clones from a HUVEC cDNA library (Edge Biosystems, Gaithersburg, MD). The "y" at position 951 of SEQ ID NO:1 represents a translationally silent C or T polymorphism, and the "y" displayed at position 2,110 of SEQ ID NO:1 represents a C or T polymorphism that can result in either a P or a S at corresponding amino acid position 704 of SEQ ID NO:2.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148-6152); gene targeting in embryonic stem cells (Thompson et al., 1989, Cell 56:313-321); electroporation of embryos (Lo, 1983, Mol Cell. Biol. 3:1803-1814); and sperm-mediated gene transfer (Lavitrano et al ., 1989, Cell 57:717-723); etc. For a review of such techniques, see Gordon, 1989, Transgenic Animals, Intl. Rev. Cytol. 115:171-229, which is incorporated by reference herein in its entirety.

The present invention provides for transgenic animals that carry the NHP transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232-6236. The regulatory sequences required for such a cell-type specific activation will depend upon the particular cell type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell type, thus inactivating the endogenous NHP gene in only that cell type, by following, for example, the teaching of Gu et al., 1994, Science, 265:103-106. The regulatory sequences required for such a cell-type specific inactivation will depend upon the particular cell type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

5.2 NHP AND NHP POLYPEPTIDES

The described NHP, NHP polypeptides, NHP peptide fragments, mutated, truncated, or deleted forms of the NHP, and/or NHP fusion proteins can be prepared for a variety of uses. These uses include, but are not limited to, the generation of antibodies, as reagents in diagnostic assays, the identification of other cellular gene products related to a NHP, as reagents in assays for screening for compounds that can be used as pharmaceutical reagents useful in the therapeutic treatment of mental, biological, or medical disorders and disease.

The Sequence Listing discloses the amino acid sequences encoded by the described NHP polynucleotides. The NHP displays an initiator methionine in a DNA sequence context consistent with a translation initiation site, and further incorporates a hydrophobic leader sequence as typically found in secreted proteins.

The NHP amino acid sequence of the invention includes the amino acid sequence presented in the Sequence Listing as well as analogues and derivatives thereof. Further, corresponding NHP homologues from other species are encompassed by the invention. In fact, any NHP product encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHP encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be a soluble or secreted molecule, the peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., E. coli, B. subtilis) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the E. coli expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101-3109; Van Heeke & Schuster, 1989, J. Biol. Chem. 264:5503-5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, Autographa californica nuclear polyhidrosis virus (AcNPV) is used as a vector to express foreign polynucleotides. The virus grows in Spodoptera frugiperda cells. A NHP coding sequence may be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted polynucleotide is expressed (e.g., see Smith et al., 1983, J. Virol. 46: 584; Smith, U.S. Pat. No. 4,215,051).

In mammalian host cells, a number of viral-based expression systems can be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655-3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516-544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972-8976). In this system, the polynucleotide of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$-nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in *Liposomes:A Practical Approach*, New,RRC ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ. This goal may be achieved by coupling of the NHP to a cytokine or other ligand that provides targeting specificity, and/or to a protein transducing domain (see generally U.S. applications Ser. No. 60/111,701 and 60/056,713, both of which are herein incorporated by reference, for examples of such transducing sequences) to facilitate passage across cellular membranes if needed and can optionally be engineered to include nuclear localization sequences when desired.

5.3 ANTIBODIES TO NHP PRODUCTS

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851-6855; Neuberger et al., 1984, Nature, 312:604-608; Takeda et al., 1985, Nature, 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150,584 and respective disclosures which are herein incorporated by reference in their entirety.

Alternatively, techniques described for the production of single chain antibodies (U.S. Pat. No. 4,946,778; Bird, 1988, Science 242:423-426; Huston et al., 1988, Proc. Natl. Acad. Sci. USA 85:5879-5883; and Ward et al., 1989, Nature 341:544-546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275-1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437-444; and Nissinoff, 1991, J. Immunol. 147(8):2429-2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP signaling pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising the nucleotide sequence of SEQ ID NO:1.

2. An isolated nucleic acid molecule comprising a nucleotide sequence encoding the amino acid sequence shown in SEQ ID NO:2.

3. An expression vector comprising a nucleic acid sequence of claim 2.

4. A cell comprising the expression vector of claim 3.

* * * * *